(12) United States Patent
Bannister et al.

(10) Patent No.: US 10,485,905 B2
(45) Date of Patent: Nov. 26, 2019

(54) FLUID COMMUNICATION PATH

(71) Applicant: Smith & Nephew PLC, Watford, Hertfordshire (GB)

(72) Inventors: Neill Philip Bannister, York (GB); Edward Yerbury Hartwell, Hull (GB); Iain Michael Blackburn, Cottingham (GB); Andrew Linton, York (GB); Mark White, Doncaster (GB); Tim Stern, Belper (GB)

(*) Notice: Subject to any disclaimer, the term of this patent is extended or adjusted under 35 U.S.C. 154(b) by 821 days.

(21) Appl. No.: 15/055,084

(22) Filed: Feb. 26, 2016

(65) Prior Publication Data

US 2016/0199551 A1 Jul. 14, 2016

Related U.S. Application Data

(62) Division of application No. 13/201,611, filed as application No. PCT/GB2010/050259 on Feb. 17, 2010, now Pat. No. 9,302,032.

(30) Foreign Application Priority Data

Feb. 19, 2009 (GB) .................................. 0902816.8

(51) Int. Cl.
*A61M 1/00* (2006.01)
*A61M 39/10* (2006.01)
(Continued)

(52) U.S. Cl.
CPC ........ *A61M 1/0084* (2013.01); *A61M 1/0023* (2013.01); *A61M 1/0088* (2013.01);
(Continued)

(58) Field of Classification Search
CPC .. A61M 1/0088; A61M 1/009; A61M 1/0092; A61M 1/0094; A61M 1/0086; A61M 1/008; A61M 1/0084
See application file for complete search history.

(56) References Cited

U.S. PATENT DOCUMENTS

| | | |
|---|---|---|
| 4,228,798 A | 10/1980 | Deaton |
| 4,382,441 A | 5/1983 | Svedman |

(Continued)

FOREIGN PATENT DOCUMENTS

| | | |
|---|---|---|
| DE | 198 44 355 | 4/2000 |
| DE | 20 2004 018 245 | 7/2005 |

(Continued)

OTHER PUBLICATIONS

International Search Report for International Application No. PCT/GB2010/050259, dated Jul. 5, 2010 in 7 pages.

*Primary Examiner* — Bradley H Philips
(74) *Attorney, Agent, or Firm* — Knobbe, Martens, Olson & Bear, LLP

(57) ABSTRACT

An apparatus and method are disclosed for providing a fluid communication path to a wound site through a drape. The apparatus comprises a body portion having a lower surface and an upper surface, at least one connection port, at least one suction port and at least one fluid communication passageway between the connection port and the suction port. A connector at an end of at least one tubular conduit is locatable through the drape into an orifice in the connection port to thereby provide a fluid communication path through the drape between the tubular conduit and the wound site.

12 Claims, 6 Drawing Sheets

(51) Int. Cl.
  *A61M 39/02* (2006.01)
  *A61M 25/02* (2006.01)
(52) U.S. Cl.
  CPC ...... *A61M 1/0092* (2014.02); *A61M 39/0247* (2013.01); *A61M 39/10* (2013.01); *A61M 39/1055* (2013.01); *A61M 2025/0266* (2013.01); *A61M 2039/1033* (2013.01)

(56) References Cited

U.S. PATENT DOCUMENTS

| | | |
|---|---|---|
| 4,969,880 A | 11/1990 | Zamierowski |
| 5,100,396 A | 3/1992 | Zamierowski |
| 5,261,893 A | 11/1993 | Zamierowski |
| 5,527,293 A | 6/1996 | Zamierowski |
| 5,549,584 A | 8/1996 | Gross |
| 5,636,643 A | 6/1997 | Argenta et al. |
| 5,645,081 A | 7/1997 | Argenta et al. |
| 6,071,267 A | 6/2000 | Zamierowski |
| 6,117,111 A | 9/2000 | Fleischmann |
| 6,135,116 A | 10/2000 | Vogel et al. |
| 6,142,982 A | 11/2000 | Hunt et al. |
| 6,345,623 B1 | 2/2002 | Heaton et al. |
| 6,398,767 B1 | 6/2002 | Fleischmann |
| 6,458,109 B1 | 10/2002 | Henley et al. |
| 6,553,998 B2 | 4/2003 | Heaton et al. |
| 6,648,862 B2 | 11/2003 | Watson |
| 6,685,681 B2 | 2/2004 | Lockwood et al. |
| 6,695,823 B1 | 2/2004 | Lina et al. |
| 6,752,794 B2 | 6/2004 | Lockwood et al. |
| 6,755,807 B2 | 6/2004 | Risk et al. |
| 6,764,462 B2 | 7/2004 | Risk, Jr. et al. |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,936,037 B2 | 8/2005 | Bubb et al. |
| 6,997,905 B2 | 2/2006 | Gillespie, Jr. et al. |
| 7,004,915 B2 | 2/2006 | Boynton et al. |
| 7,022,113 B2 | 4/2006 | Lockwood et al. |
| 7,070,584 B2 | 7/2006 | Johnson et al. |
| 7,108,683 B2 | 9/2006 | Zamierowski |
| 7,117,869 B2 | 10/2006 | Heaton et al. |
| 7,195,624 B2 | 3/2007 | Lockwood |
| 7,198,046 B1 | 4/2007 | Argenta |
| 7,216,651 B2 | 5/2007 | Argenta et al. |
| 7,316,672 B1 | 1/2008 | Hunt et al. |
| 7,338,482 B2 | 3/2008 | Lockwood et al. |
| 7,438,705 B2 | 10/2008 | Karpowicz et al. |
| 7,524,315 B2 | 4/2009 | Blott et al. |
| 7,534,240 B1 | 5/2009 | Johnson |
| 7,534,927 B2 | 5/2009 | Lockwood |
| 7,615,036 B2 | 11/2009 | Joshi et al. |
| 7,651,484 B2 | 1/2010 | Heaton et al. |
| 7,699,830 B2 | 4/2010 | Blott et al. |
| 7,776,028 B2 | 8/2010 | Miller et al. |
| 7,779,625 B2 | 8/2010 | Joshi et al. |
| 7,794,450 B2 | 9/2010 | Blott et al. |
| 7,909,805 B2 | 3/2011 | Weston |
| 7,922,703 B2 | 4/2011 | Riesinger |
| 7,964,766 B2 | 6/2011 | Blott et al. |
| 8,002,313 B2 | 8/2011 | Singh et al. |
| 8,062,272 B2 | 11/2011 | Weston |
| 8,128,607 B2 | 3/2012 | Hu et al. |
| 8,128,615 B2 | 3/2012 | Blott et al. |
| 8,152,785 B2 | 4/2012 | Vitaris |
| 8,162,907 B2 | 4/2012 | Heagle |
| 8,162,908 B2 | 4/2012 | Hu et al. |
| 8,177,764 B2 | 5/2012 | Hu et al. |
| 8,246,591 B2 | 8/2012 | Braga et al. |
| 8,308,703 B2 | 11/2012 | Heaton et al. |
| 8,398,614 B2 | 3/2013 | Blott et al. |
| 8,535,296 B2 | 9/2013 | Blott et al. |
| 8,715,256 B2 | 5/2014 | Greener |
| 8,734,410 B2 | 5/2014 | Hall et al. |
| 8,758,328 B2 | 6/2014 | Locke et al. |
| 8,764,732 B2 | 7/2014 | Hartwell |
| 8,784,393 B2 | 7/2014 | Weston et al. |
| 8,795,243 B2 | 8/2014 | Weston |
| 8,808,274 B2 | 8/2014 | Hartwell |
| 8,834,451 B2 | 9/2014 | Blott et al. |
| 8,843,327 B2 | 9/2014 | Vernon-Harcourt et al. |
| 8,882,746 B2 | 11/2014 | Blott et al. |
| 8,926,592 B2 | 1/2015 | Blott et al. |
| 2002/0065494 A1 | 5/2002 | Lockwood et al. |
| 2002/0115952 A1 | 8/2002 | Johnson et al. |
| 2002/0161346 A1 | 10/2002 | Lockwood et al. |
| 2003/0040687 A1 | 2/2003 | Boynton et al. |
| 2003/0219469 A1 | 11/2003 | Johnson et al. |
| 2005/0004534 A1 | 1/2005 | Lockwood et al. |
| 2005/0085795 A1 | 4/2005 | Lockwood |
| 2005/0090787 A1 | 4/2005 | Risk, Jr. et al. |
| 2006/0029675 A1 | 2/2006 | Ginther |
| 2006/0149171 A1 | 7/2006 | Vogel et al. |
| 2007/0014837 A1 | 1/2007 | Johnson et al. |
| 2007/0021697 A1 | 1/2007 | Ginther et al. |
| 2007/0219512 A1 | 9/2007 | Heaton et al. |
| 2008/0011368 A1 | 1/2008 | Singh et al. |
| 2008/0208171 A1* | 8/2008 | Argenta ............ A61M 1/0088 604/540 |
| 2009/0227968 A1 | 9/2009 | Vess |
| 2009/0234309 A1 | 9/2009 | Vitaris et al. |
| 2009/0240218 A1 | 9/2009 | Braga et al. |
| 2009/0275884 A1 | 11/2009 | McNulty et al. |
| 2009/0281526 A1 | 11/2009 | Kenny et al. |
| 2009/0299251 A1 | 12/2009 | Baun |
| 2009/0312727 A1 | 12/2009 | Heaton |
| 2010/0106114 A1 | 4/2010 | Weston et al. |
| 2010/0228205 A1 | 9/2010 | Hu et al. |
| 2010/0228206 A1 | 9/2010 | Larsson |
| 2010/0305524 A1 | 12/2010 | Vess et al. |
| 2011/0009838 A1 | 1/2011 | Greener |
| 2011/0028917 A1 | 2/2011 | Hall et al. |
| 2011/0301557 A1 | 12/2011 | Singh et al. |
| 2012/0078207 A1 | 3/2012 | Hu et al. |
| 2012/0209225 A1 | 8/2012 | Hu et al. |
| 2013/0096519 A1 | 4/2013 | Blott et al. |
| 2013/0267921 A1 | 10/2013 | Weston |
| 2014/0330225 A1 | 11/2014 | Hall et al. |
| 2014/0343519 A1 | 11/2014 | Weston |
| 2015/0080787 A1 | 3/2015 | Blott et al. |

FOREIGN PATENT DOCUMENTS

| | | | |
|---|---|---|---|
| DE | 10 2005 010419 A1 | 9/2006 | |
| FR | 1163907 | 10/1958 | |
| GB | 2 356 148 A | 5/2001 | |
| WO | WO 2003/057307 | 7/2003 | |
| WO | WO 2003/073970 | 9/2003 | |
| WO | WO 2007/050594 | 5/2007 | |
| WO | WO 2007/092397 | 8/2007 | |
| WO | WO 2007/133644 | 11/2007 | |
| WO | WO-2008014358 A2 * | 1/2008 | .......... A61M 1/0088 |
| WO | WO 2008/027449 | 3/2008 | |
| WO | WO 2008/041926 | 4/2008 | |
| WO | WO 2008/131896 | 11/2008 | |
| WO | WO 2009/070905 | 6/2009 | |
| WO | WO 2009/103031 | 8/2009 | |
| WO | WO 2010/094957 | 8/2010 | |

* cited by examiner

FLUID COMMUNICATION PATH

CROSS-REFERENCE TO RELATED APPLICATIONS

This application is a divisional of U.S. patent application Ser. No. 13/201,611 published on Jun. 7, 2012 as US 2012/0143156 A1, which is a U.S. National Phase of PCT International Application No. PCT/GB2010/050259, filed on Feb. 17, 2010, designating the United States and published on Aug. 26, 2010 as WO 2010/094957, which claims priority to Great Britain Patent Application No. 0902816.8, filed on Feb. 19, 2009.

BACKGROUND OF THE DISCLOSURE

Field of the Invention

The present invention relates to an apparatus and method for providing negative pressure at a wound site. In particular, but not exclusively, the present invention relates to apparatus for connecting a source of negative pressure to a wound site via a fluid communication path completed when a drape covering the wound site is pierced.

Background

Devices for the generation of negative pressure at the surface of skin have been used for many hundreds of years to treat animal and human bodies. For example the cupping technique (which relates to the positioning of a mouth of a rigid vessel containing hot air) is a well known technique. Spring powered syringes and suction cups are other mechanical techniques which have been used in the past for generating a vacuum on tissue. In common with cupping such techniques have, in the past, suffered from a very limited longevity of the therapy which can be applied. That is to say the duration of the negative pressure which can be maintained over a site of application has been limited.

To enable a more prolonged application of controlled negative pressure, powered systems, which include a vacuum generation source such as a pump of some type have been developed and many examples of such systems are used today for the management of wounds. However, many of these systems are not convenient for a user trying to provide a fluid communication path between the vacuum generation source and wound site.

For example, one technique which is known is to provide a tubular conduit from the vacuum generation source to a drape covering a wound site. The drape which acts as a sealed covering over the wound site is pinched around the tubular conduit which passes thereunder. An adhesive lower surface of the drape is secured to a peripheral region around a wound site and the tubular conduit. Whilst providing a technique which is straightforward to use such fastenings are prone to leakage paths being formed which can degrade the negative pressure applied at the wound site over time.

Other techniques have been proposed for dressing a wound site in a sealed manner which enables a negative pressure to be established over the wound and provides a fluid communication path through the drape. One such technique is to cut the drape, for example by pinching the drape and then cutting through a small portion of it. However, the size of opening so formed in the drape is difficult to control and if a small orifice is required such an orifice is prone to being lost or misaligned subsequent to cutting as it can be visually difficult to discern the location of the small cut opening after its generation.

SUMMARY OF SOME EXEMPLIFYING EMBODIMENTS

It is an aim of the present invention to at least partly mitigate the above-mentioned problems.

It is an aim of certain embodiments of the present invention to provide an apparatus which can be operated in a manner which is not prone to user error and which conveniently provides a pierced hole and associated fluid communication path through a drape at a desired location.

It is an aim of certain embodiments of the present invention to provide a kit of parts which can be provided to a user to enable that user to conveniently dress and subsequently treat a wound.

It is an aim of certain embodiments of the present invention to provide a system for applying negative pressure at a wound site with a risk of leakage being reduced with respect to prior art techniques.

According to a first aspect of the present invention there is provided apparatus comprising a body portion locatable under a drape covering a wound site for providing a fluid communication path to the wound site through the drape, the body portion comprising:
  a lower surface and an upper surface for supporting an overlying region of a drape;
  a connection port comprising an orifice in the upper surface of the body portion;
  at least one suction port locatable in fluid communication with the wound site; and
  a fluid communication passageway between the connection port and the suction port; wherein
  a connector at an end of a tubular conduit is locatable through the drape into the orifice to thereby provide a fluid communication path through the drape between the tubular conduit and the wound site.

According to a second aspect of the present invention there is provided a connector for providing a fluid communication path through a drape covering a wound site, comprising:
  a body portion comprising a first end arranged to be connected to a tubular conduit, a remainder end region comprising a one of a piercing member or a piercing member receptor, and a fluid communication passageway extending between the first end and the remainder end region; wherein
  the connector is locatable through a portion of a drape covering a connection port of a body portion underlying an overlying region of the drape, location of the connector piercing the drape and completing a fluid communication path through the drape between the tubular conduit and a suction port of the body portion in fluid communication with a wound site underlying the drape.

According to a third aspect of the present invention there is provided a kit of parts comprising:
  the apparatus as claimed in any one of claims 1 to 13 of PCT Application NO. PCT/GB2010/050259 as filed; and
  at least one connector as claimed in any one of claims 14 to 18 of PCT Application No. PCT/GB2010/050259 as filed.

According to a fourth aspect of the present invention there is provided a method for providing a fluid communication path through a drape covering a wound site, comprising the steps of:
  locating a body portion comprising a lower surface and an upper surface for supporting an overlying region of a drape at a selected location with respect to a wound site;
  covering the body portion and wound site with a drape; and
  locating a connector into an orifice of a connection port of the body portion through a portion of the drape thereby completing a fluid communication path through the drape between a tubular conduit terminated by the connector and a suction port of the body portion in fluid communication with the wound site.

Certain embodiments of the present invention enable a user to locate a drape support component over or adjacent to a wound site. A drape is then placed over the component body and then punctured via a connector urged into an opening of the component body. The body includes one or more open passageways which enable a fluid communication path to be completed between a vacuum generation source connected to the connector and the wound site. By puncturing the drape simultaneously with generating a fluid communication path for negative pressure therapy a risk of hole misalignment or loss is much reduced.

Certain embodiments of the present invention enable a drain to be very conveniently connected through a drape to a vacuum generation source.

Certain embodiments of the present invention provide a method and apparatus which is not prone to human error.

BRIEF DESCRIPTION OF THE DRAWINGS

Embodiments of the present invention will now be described hereinafter, by way of example only, with reference to the accompanying drawings in which.

DETAILED DESCRIPTION OF SOME EXEMPLIFYING EMBODIMENTS

Figure 1:
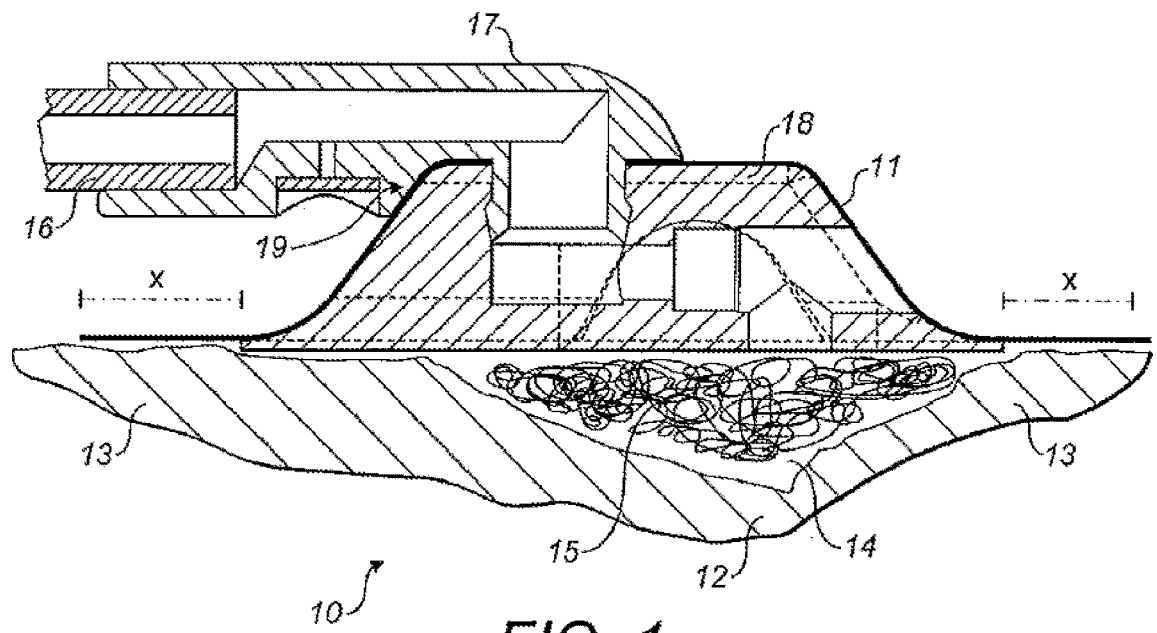
FIG. 1 illustrates a fluid communication path through a drape.

FIG. 1 illustrates a location 10 where topical negative wound therapy (NPWT) is to be applied at a wound site. FIG. 1 illustrates a view of a drape 11 which, in use, is located over and around a wound site 12. The drape 11 acts as a dressing covering the wound and may be any type of dressing normally employed with NPWT and, in very general terms, may comprise, for example a semi-permeable flexible, self-adhesive drape material as is known in the dressings art to cover the wound and seal with surrounding sound tissue 13 to create a sealed cavity or void over the wound. This sealed cavity or void is referred to hereinafter as a wound chamber 14. Hereinafter a chamber is taken to mean an enclosed volume of any geometry. The chamber may be of fixed or flexible geometry.

As illustrated in FIG. 1 wound packer material 15 may be used in the cavity between a wound bed and the drape to help enable an even vacuum distribution to be achieved over the area of the wound. The packer material can be any suitable material as will be understood by those skilled in the art. For example, a foam or gauze material resistant to pressure under the levels of vacuum created and which permits transfer of wound exudate across the wound area can be used. The wound packer helps resist crushing under the levels of vacuum created at the wound site and permits transfer of wound exudates across the wound area to a suction tube 16 sealed to the flexible cover drape which extends over the wound.

The suction tube may be a plain flexible tube, for example, having a single lumen therethrough and made from a plastics material compatible with raw tissue. However, the aspiration conduit may alternatively have a plurality of lumens therethrough to achieve specific objectives.

It is envisaged that the negative pressure range for the apparatus embodying the present invention may be between about −50 mmHg and −200 mmHg (note that these pressures are relative to normal ambient atmospheric pressure thus, −200 mmHg would be around 560 mmHg in practical terms). Aptly, the pressure range may be between about −75 mmHg and −150 mmHg. Alternatively a pressure range of up to −75 mmHg, up to −80 mmHg or over −80 mmHg can be used. Also aptly a pressure range of below −75 mmHg could be used. Alternatively a pressure range of over −100 mmHg could be used or over −150 mmHg. Aptly the pressure of the wound chamber is between −125 mmHg and −20 mmHg. It will thus be appreciated that negative pressure is taken to mean a pressure that is less than ambient atmospheric pressure.

An end of the suction tube 16 is terminated in a connector 17 which in use is urged into an opening in an upper surface of a body 18 which supports the drape 11.

Figure 2:
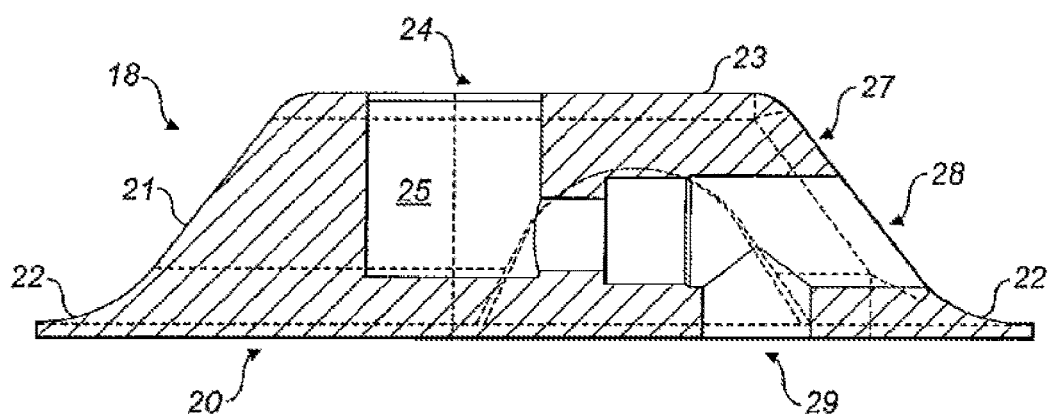
FIG. 2 illustrates a body used to support a drape.

FIG. 2 illustrates the drape support component 18 in more detail. The body of the component has a lower substantially planar surface 20 upon which the body 18 rests in use. The lower surface can include adhesive regions or can wholly be covered by an adhesive layer to aid fixing the body at a desired location with respect to the wound site. The lower base surface 20 can be duly located on an area of skin 13 surrounding a wound site or alternatively partially or fully over wound packer material 15. An upper surface of the body 18 is provided by an upwardly and inwardly extending side wall 21 which extends smoothly from a peripheral lip region 22 into a top surface area 23. The peripheral lip helps provide a gradual support for the drape as it curves upwards and thus reduces the risk of tearing. Also use of a lip helps maximise a cross section of the base of the body which spreads any loads generated when a patient turns and lies on the dressing and body.

Figure 3:
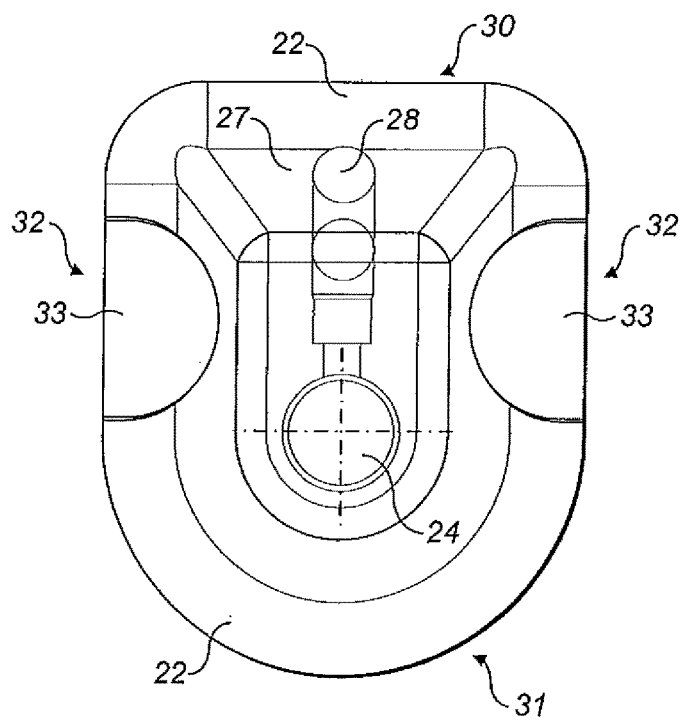
FIG. 3 illustrates another view of the body in FIG. 2.

FIG. 3 illustrates a top view of the body shown in FIG. 2. As illustrated in FIG. 3 the body has a generally D-shape having a substantially straight edge 30 and a spaced apart curved edge 31 separated by linear sides 32. A lip 22 extends circumferentially around the whole of the body. The body is integrally formed from a resilient material having a type A Shore hardness of greater than around 10 and a type A Shore hardness of less than around 70. It will be appreciated that according to certain other embodiments of the present invention the body may be formed from a material or a combination of materials having different hardnesses. Likewise certain embodiments of the present invention may utilise a body which is not integrally formed. Indents 33 on the two sides 32 increase the ease by which the body may be picked up and located by a user. By pinching the indents the resilience of the material is such that the body is effectively squeezed between finger and thumb and can then be duly located at a desired location with respect to a wound site. The indents also allow the drape and body to be held up away from a patient's body whilst the drape is punctured by connecting the connector to the body. This helps reduce patient discomfort.

As illustrated in FIG. 2 an orifice 24 is formed in the top surface 23 the upwards facing surface of the body 18. The orifice 24 presents an open mouth on an upper surface of the body which in use will receive the connector 17. A chamber 25 extends into the body from the open mouth and a master passageway extends horizontally from the chamber 25 to a region of a side wall 27. An opening 28 in the side wall forms a first suction port. A further suction port is formed in the lower surface 20. The lower surface suction port 29 is connected to the master passageway via a downwardly extending slave passageway. The side suction port and lower surface suction port are in fluid communication with the mouth 24 on the top surface of the body via the chamber 25 and connecting passageways.

It will be understood that according to certain embodiments of the present invention the body may be provided with only the bottom surface suction port 29 or only the side wall suction port 28 or both a lower surface suction port 29 and side suction port 28 or more than one side suction port and/or more than one lower surface suction port.

Figure 4:
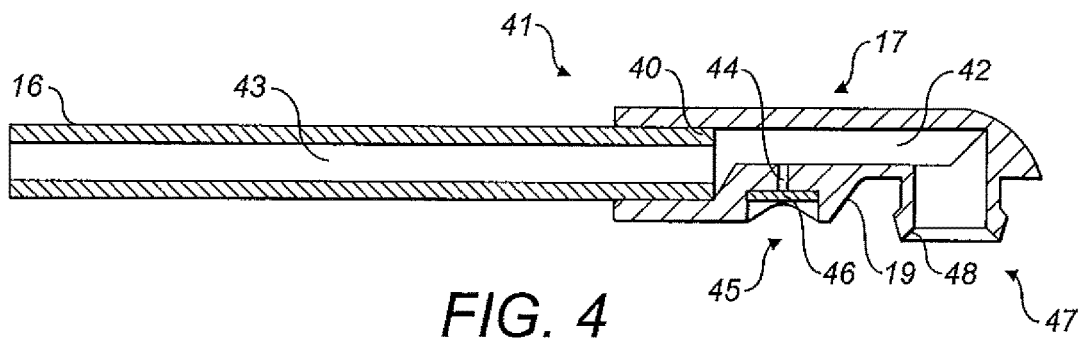
FIG. 4 illustrates a section through a connector and tubing.

FIG. 4 illustrates how a suction tube 16 has an end 40 terminated in a connector 17. The connector 17 is an elongate integrally formed piece of semi-rigid material having a type A Shore hardness of greater than around 90. It will be appreciated that according to certain embodiments of the present invention a rigid material such as metal or other such material type could be used. Also the connector could be formed in more than one piece and be fitted together. At a first end region 41 of the connector 17 an opening is formed having an inner diameter configured to receive the end 40 of the conduit 16. A substantially D-shaped passageway 42 in fluid communication with the internal bore 43 of the conduit 16 extends along the longitudinal length of the connector 17. This helps match the cross section in the passageway to the cross sectional area in the bore of the conduit 16. A bleed port 44 extends from a region of a side of the passageway 42 and an outer recess 45 in the body of the connector 17 holds a filter 46 which prevents contaminants exiting or gaining ingress into the fluid communication path. An end of the connector distal to the tubular conduit 16 provides a mouth region 47. A passageway leading into the mouth region 47 has a longitudinal axis substantially perpendicular to the longitudinal axis of the passageway 42 leading to the tubular conduit 16. A piercing tip 48 is formed as a rim extending around the mouth 47 of the connector. The body of the connector extending backwardly from the cutting edge rim 48 extends outwardly in a flared snap fit configuration.

Figures 5A, 5B:
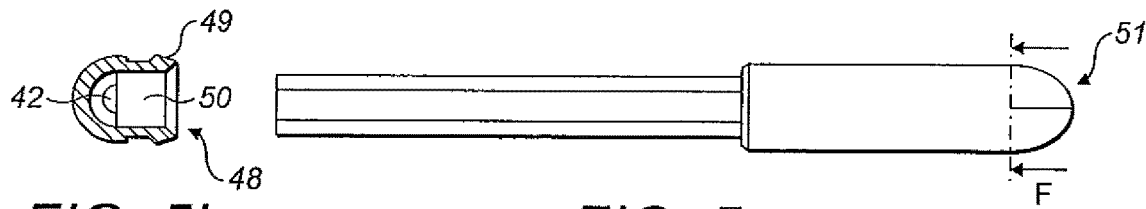
FIG. 5A illustrates a top view of a connector and tubing.
FIG. 5B illustrates a cross section through an end region of a connector.

FIG. 5A illustrates a top, non cutaway, view of the connector 17 and tube 16. FIG. 5B illustrates a cutaway view of the end shown by arrows F in FIG. 5A and illustrates the D-shaped passageway 42 and how this opens into a mouth region 50 at the end region 51 of the connector. FIG. 5B also illustrates the cutting rim 48 and outer conically extending surface 49 which enables the connector in use to cut through a drape and snap fit into the connection port 24 formed on the upper surface of the body 18.

Figure 6:
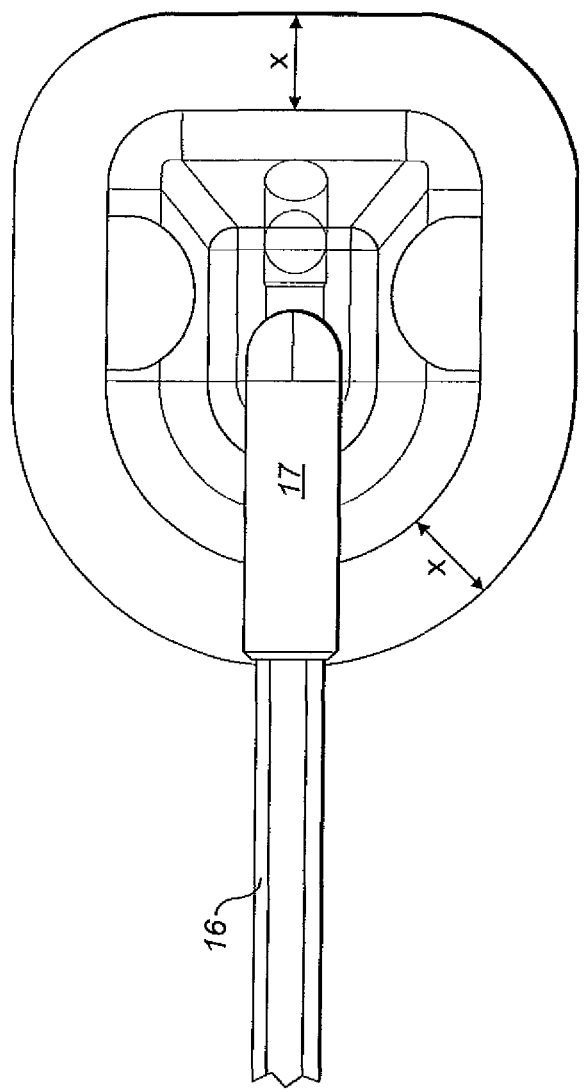
FIG. 6 illustrates a top view of a connector secured to a drape covering a wound site.

FIG. 6 illustrates how a fluid communication path can be provided between a wound site through a drape to a negative pressure source. During use the body 18 is located over or close to a wound site 12. This is achieved by a user pinching the body between thumb and forefinger and duly locating the body so that the lower surface 20 of the body rests on the wound packer 15 and/or surrounding sound tissue 30. As illustrated in FIG. 1 a suction port 29 on the lower surface of the body is in fluid communication with the wound packer 15 and thus the target wound site 12. A drape is then located over the body 18. Prior to location a lower surface of the drape has a cover layer removed to reveal a lower adhesive surface. As illustrated in FIG. 6 the outer periphery, that is to say shape, of the drape is selected so as to extend at least a predetermined distance x beyond the lip 22 of the body 18. It will be appreciated that the shape of the drape does not need to match the shape of the component body but this is convenient to ensure a desired amount of drape extends beyond the lip of the body to provide a good seal around the wound site. The upper surface of the body formed by the upwardly facing top surface 23 and side walls 21 and lip 22 thus support the dressing in a smooth way so that no tearing or cutting occurs to the drape. This retains the integrity of the drape so that a wound chamber therebelow can be evacuated to apply negative pressure at the wound site. It is to be noted that the drawings are not shown to scale but rather are included for the purposes of illustration only. In this sense the wound site may be considerably larger than the size of the body. A drape will extend a distance x well beyond the extremities of the body. The body may be located centrally or off centre with respect to the drape.

A suction tube 16 having a connector 17 on an end thereof is connected to a negative pressure source such as a vacuum pump. A user locates the connector 17 above the orifice 24 which is aptly visible or semi-visible through the drape covering grips the indents of the body and the drape and then in a single motion pushes the connector 17 towards the drape and body so that the piercing rim 48 and snap fit connector of the connector are thrust through the drape into the orifice. The piercing rim 48 pierces the drape and simultaneously completes a fluid communication path with the conduit 16 and the side suction port 28 and bottom suction port 29. It is to be noted that as the piercing rim of the connector is urged into the body, drape material which is punched through tends to accumulate between the outer surface of the connector and the body 18. This, together with the inner dimensions of the chamber 25 and outer dimensions of the connector 17, produces a fluid-tight seal. It will be appreciated that the resilient body 18 can be manufactured with an undersized opening 24 and chamber 25 to enhance the sealing effect.

Once the connector 17 is connected to the body a negative pressure can be applied to the wound site as will be appreciated by those skilled in the art. Fluid, including possibly wound exudate, is drawn through the lower surface suction port from the wound site and wound packer into the conduit 16 and to the remote pump.

The connector 17 can, to a certain extent, swivel in the chamber 25 in the body 18. This provides the advantage that when a patient moves the conduit and connector can move accordingly to a certain extent to prevent disconnection and to improve comfort to the patient. As illustrated in FIGS. 1 and 6 the extent of swivelling which can take place about an axis centred through the chamber 25 is limited by the curved surface of the body 18 and an outer surface 19 which rides proximate to the drape. This riding surface 19 eventually abuts the linear side surface of the drape and body effectively providing 180° of swivel. It will be appreciated that if the body were formed in a circular shape then the connector could swivel through 360°. Swivelling can be wholly prevented or an allowable angle controlled by providing a more rigid housing in the body with one or more abutment faces contacting corresponding abutment faces on the piercing stem of the connector.

It will be appreciated that whilst the above-mentioned embodiment is described as having a piercing rim on the connector, certain other embodiments of the present invention could utilise a piercing rim or other shaped member in the recessed body with the connector being used to urge the drape into a recess where the piercing member is located.

Figure 7:
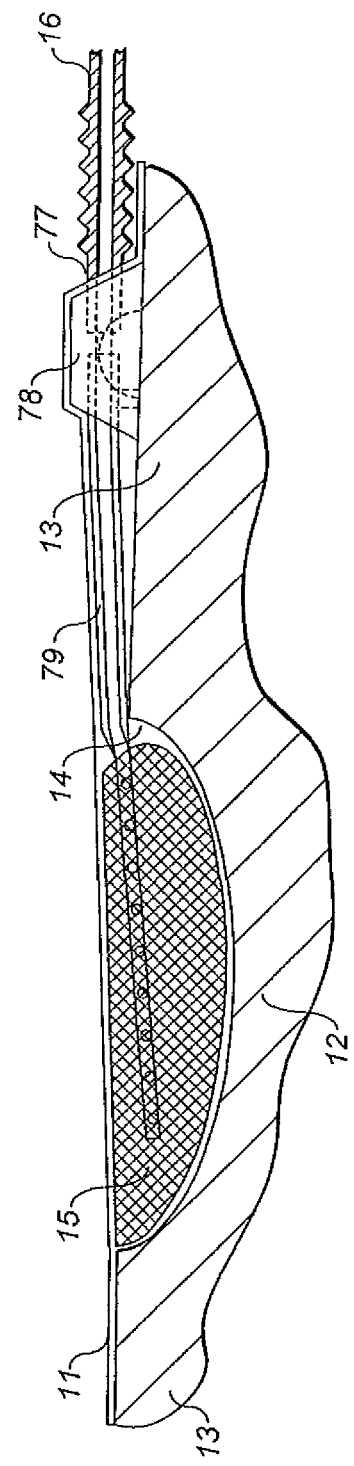
FIG. 7 illustrates a fluid communication path through a drape.

FIG. 7 illustrates an alternative embodiment of the present invention. In contrast to the embodiment illustrated with respect to FIGS. 1 to 6, the embodiment shown in FIGS. 7 to 10 illustrate how a connector 77 can be connected sideways into a side wall of a body 78. This embodiment does not enable the connector to swivel with respect to the body as described in the previous embodiment.

A drape 11 is located over a wound site 12. The drape covers the wound site 12 and is secured to sound tissue 13 to create a sealed cavity or void over the wound. This sealed cavity or void is referred to hereinafter as a wound chamber 14.

Wound packer material 15 may be used in the cavity between a wound bed and the drape to help enable an even vacuum distribution to be achieved over the area of the wound.

A drain 79 is illustrated secured to a side suction port of the body 78. The wound drain 79 is an elongate flexible tube which can be located in a target wound site. The wound drain can be of any type known in the art, such as a channel wound drain or flat wound drain. It will be appreciated that the embodiment shown in FIG. 7 is utilised with the body 78 resting on sound skin 13 close to a wound site. The drain 79 is located under the drape. It will be appreciated that a drain may aptly be used with the other embodiments described hereinbefore and hereinafter.

Figure 8A:
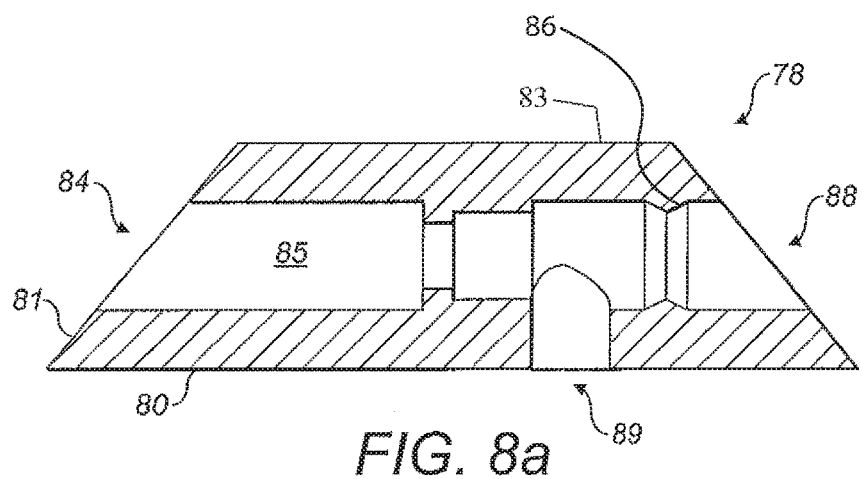
FIGS. 8a and 8b illustrate a body used to support a drape.
Figure 8B:
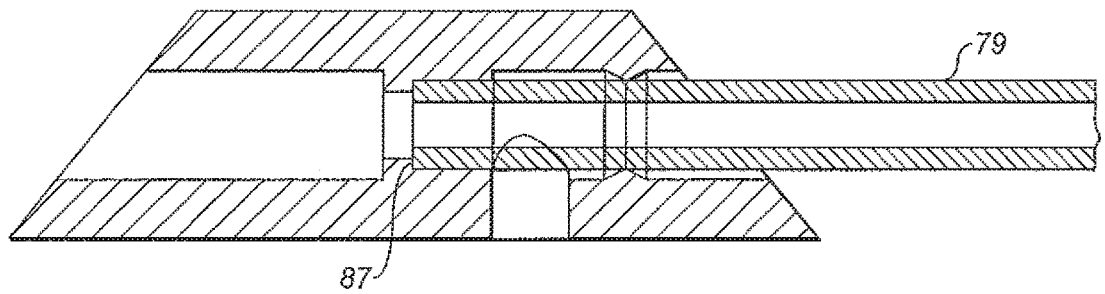

FIGS. 8a and 8b illustrate the body 78 shown in FIG. 7 in more detail. The body 78 is used as a drape support component and has a lower substantially planar surface 80 upon which the body 78 rests in use. The lower surface can include adhesive regions or can wholly be covered by an adhesive to aid fixing the body at a desired location with respect to a wound site. An upper surface of the body 78 is provided by an upwardly and inwardly extending side wall 81. It is to be noted that in this embodiment no lip is shown although the body 78 could, of course, be modified to include a lip as described hereinabove with respect to the previous embodiment. The body 78 has a substantially straight crest 83.

FIG. 8a in particular illustrates how a pinch seal 86 can be provided in the passageway extending from the opening 88. This is achieved either by providing a closing of the internal diameter of the bore (such a narrowing pinches on the outer surface of the drain) or by providing a recessed ring in which an "o" ring seal can be located. In this way as illustrated in FIG. 8b when a drain 79 is urged through the opening 88 against a drain seat 87 the pinch seal 86 seals against an outer diameter of the drain. The end of the drain which is urged against the drain seat 87 is sealed in this way so that fluid communication only occurs through the chamber 85 into the inner diameter bore of the drain 79. This drain seal 87 and the pinch seal 86 effectively close off the orifice 89 on the lower surface 80 of the body.

Figure 9:
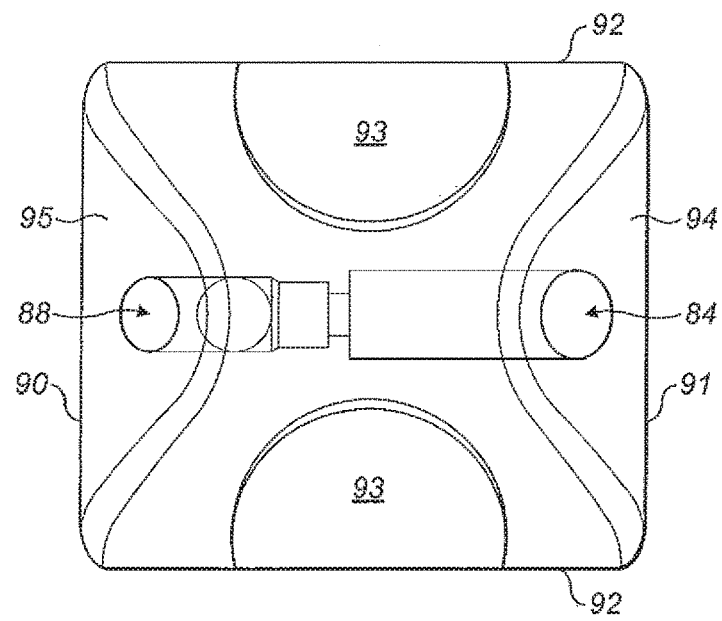
FIG. 9 illustrates another view of the body shown in FIGS. 8a and 8b.

FIG. 9 illustrates a top view of the body 78 shown in FIGS. 8a and 8b. As illustrated in FIG. 9 looked at from above the body 78 has a generally rectangular shape having a substantially straight edge 90 and a spaced apart straight edge 91 separated by linear sides 92. The body is integrally formed from a resilient material having a type A Shore hardness of greater than around 10 and a type A Shore hardness of less than around 70. It will be appreciated that according to certain other embodiments of the present invention the body may be formed from a material or a combination of materials having different hardnesses. Likewise certain embodiments of the present invention may utilise a body which is not integrally formed. Indents 93 on the two sides 92 increase the ease by which the body may be picked up and located by a user. By pinching the indents the resilience of the material is such that the body is effectively squeezed by finger and thumb of a user and can then be duly located at a desired location with respect to a wound site. Also the indents allow the drape and body to be held up away from a patient's body whilst a drape is punctured by connecting the connector through the drape to the body. This helps reduce patient discomfort.

As illustrated in FIGS. 8a and 8b an orifice 84 is formed in an end surface 94 extending upwardly from an edge 91 of the body 78. The orifice 84 presents an open mouth on an upper surface of the body which in use will receive the connector 77. A chamber 85 extends into the body from the open mouth and a master passageway extends horizontally from the chamber 85 to a region of an end wall 95 extending upwards from an edge 90 of the body. An opening 88 in the side wall forms a first suction port. A further suction port 89 is formed in the lower surface 80. The side suction port and lower surface suction port are in fluid communication with the mouth 84 on the side of the body via the chamber 85 and connecting passageways.

It will be understood that according to certain embodiments of the present invention the body may be provided with only the bottom surface suction port or only the side wall suction port 88 or both a lower surface suction port and side suction port or more than one side suction port and/or more than one lower surface suction port.

Figure 10:
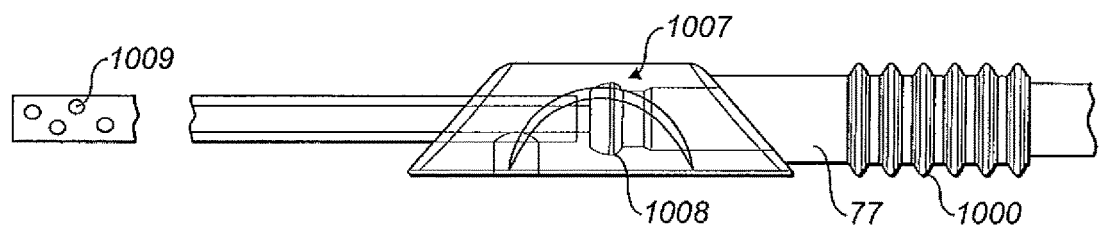
FIG. 10 illustrates a connector and drain in fluid communication.

FIG. 10 illustrates how a suction tube 16 has an end terminated in the connector 77. The connector 77 is an elongate integrally formed piece of semi-rigid material having a type A Shore hardness of greater than around 90. It will be appreciated that according to certain embodiments of the present invention a rigid material, such as metal or the like, could be used. Also the connector could be formed in more than one piece and be fitted together. An external surface of the connector 77 has six circumferentially extending ribs 1000 which enable a user to more readily grasp the connector. A passageway in the connector 77 is in fluid communication with an internal bore 43 of the suction tube 16. An end of the connector distal to the suction tube 16 provides a mouth region 1007 in line with the longitudinal axis of the connector. A piercing tip 1008 is formed as a rim extending around the mouth 1007 of the connector. The body of the connector extends backwards from the cutting edge rim extends outwardly in a flared snap fit configuration.

FIG. 10 also helps illustrate how a fluid connection path can be provided between a wound site through a drape to a negative pressure source. During use the body 78 is located close to a wound site 12. This is achieved by a user pinching the body between thumb and forefinger and duly locating the body so that a lower surface 80 of the body rests on sound tissue. A drain which may include perforations 1009 at a distal end thereof is located in the wound site and a drape is located over the body and drain and wound site. As noted above a lower adhesive surface of the drape may be revealed by being uncovered prior to such location. The upper surface of the body 78 formed by the upwardly facing end walls, side wall and crest thus support the dressing in a smooth way so that no tearing or cutting occurs to the drape. This retains the integrity of the drape so that a wound chamber defined under the drape can be evacuated to apply negative pressure at the wound site.

A suction tube 16 having a connector 77 on an end thereof is connected to a negative pressure source such as a vacuum pump. A user locates the connector 77 close to the orifice 84 which is aptly visible or semi-visible through the drape covering, grips the indents of the body and thus the drape and then in a single motion pushes the connector 77 towards the drape and body so that the piercing rim 1008 and snap fit connector end of the connector 77 are thrust through the drape into the orifice. The piercing rim 1008 pierces the drape and simultaneously completes a fluid communication path with the suction tube 16 and the side suction port 88. It is to be noted that as the piercing rim of the connector is urged into the body, drape material which is punched through tends to accumulate between an outer surface of the connector and the body 78. This, together with the inner dimensions of the chamber 85 and outer dimensions of the connector 1007, produces a fluid-tight seal. It will be appreciated that the resilient body 78 can be manufactured with an undersized opening 84 and chamber 85 to enhance the sealing effect.

It is to be noted that as an end of the drain is located in the side suction port of the body 78 the drain can be driven into the body until an end of the drain abuts with a drain seat region. This indicates to a user that the drain is fully in place. The internal diameters of the lower suction port 89 are such that when a drain is so located an outer surface of the drain tube seals the lower suction port 89 closed. As such a fluid communication path passes substantially horizontally as shown in FIG. 7.

An advantage of providing a body 78 having at least one side suction port and at least one lower surface suction port is that a single body can be utilised for a variety of purposes, for example with the drain tube shown in respect of FIGS. 7 to 9 or for use over a target wound site as described with respect to FIGS. 1 to 6. This reduces inventory at the premises of a user since specialised bodies do not need to be stored for separate purposes.

Once the connector 77 is connected to the body a negative pressure can be applied to the wound site as will be appreciated by those skilled in the art. Fluid, including possibly wound exudate, is drawn through the end of the drain and/or perforations 1009 in the drain into the passageway extending through the body and into the internal bore of the connector and suction tube 16.

Figure 11:
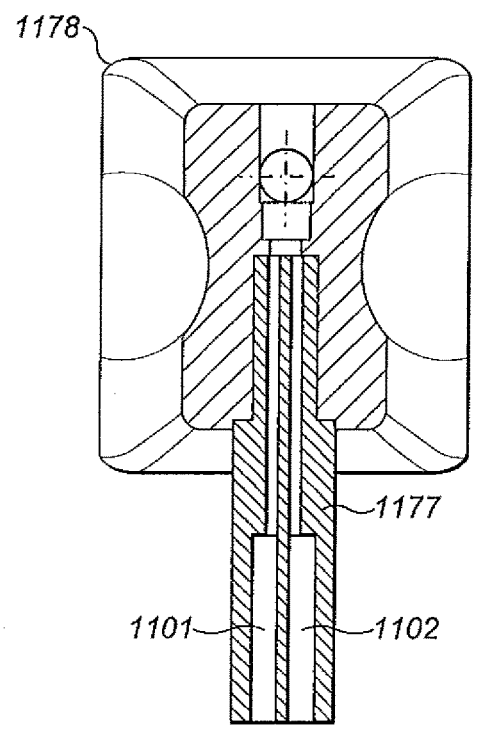
FIG. 11 illustrates a connector located in a body.
Figure 12:
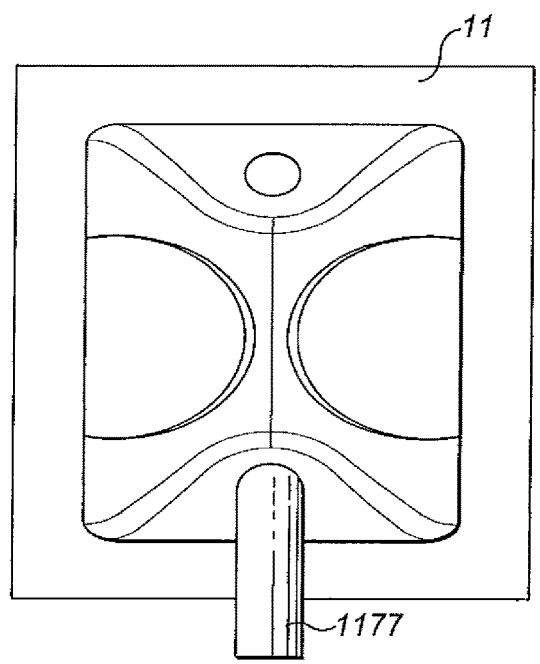
FIG. 12 illustrates a drape overlying a body with a connector secured therein.

FIG. 11 illustrates how a dual lumen 1101, 1102 suction tube is terminated in a single connector 1177. Dual lumens are useable for a wide variety of uses, for example for the introduction of irrigation fluid or agents to a wound site and/or for the application of negative pressure and/or for the measuring of negative pressure provided at a wound site. The connector 1177 is an elongate integrally formed piece of semi-rigid material having a type A Shore hardness of greater than around 90. It will be appreciated that according to certain embodiments of the present invention a rigid material, such as metal or the like could be used. Also the connector can be formed in one or more piece fitted together. The connector is illustrated connected through an opening into a body 1178. FIG. 12 illustrates in use how a drape 11 may be placed over the body 1178 and then the connector 1177 pushed through the drape through an opening in the body 1178.

Figure 13:
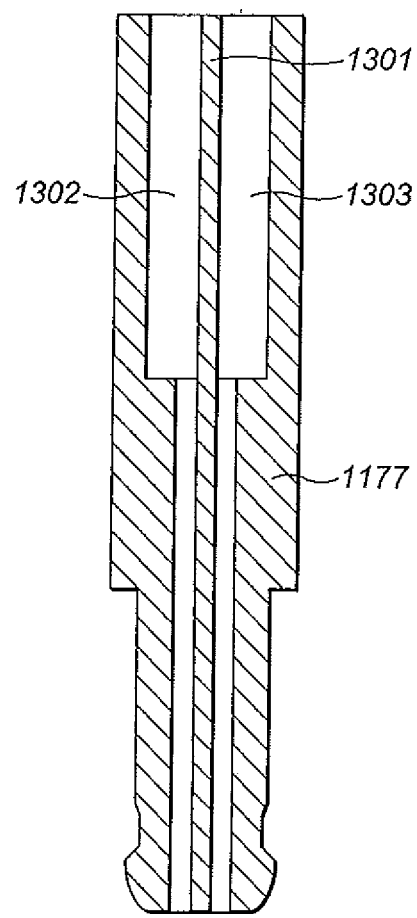
FIG. 13 illustrates a multi passageway connector.
Figure 14:
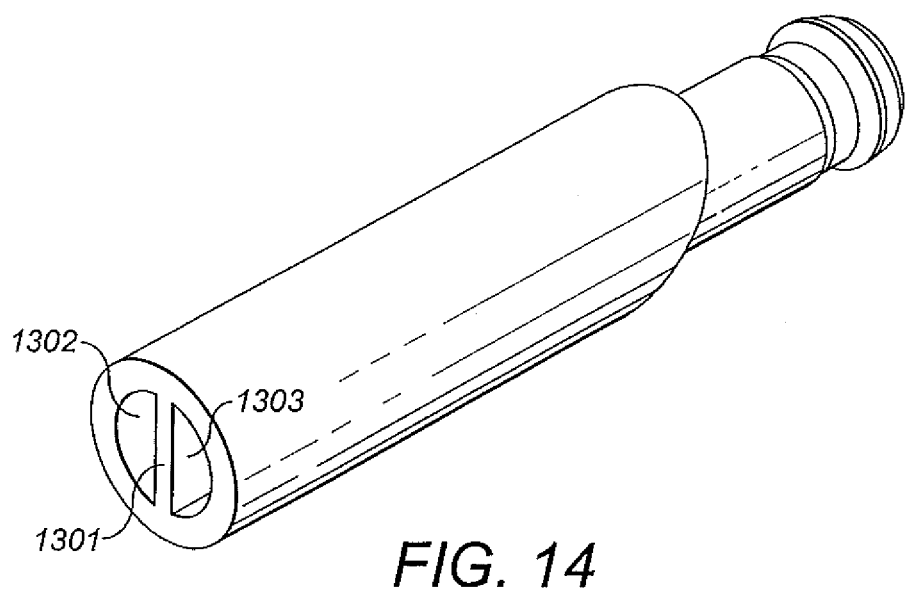
FIG. 14 illustrates a multi passageway connector.
  In the drawings like reference numerals refer to like parts.

FIG. 13 illustrates how the body of the connector 1177 has a central longitudinally extending dividing wall 1301. The dividing wall 1301 extends along the whole length of the connector 1177. A first passageway 1302 is defined on one side of the dividing wall 1301 and a first lumen can be duly located in an open mouth thereof. The lumen is in fluid communication with the passageway 1302. A further passageway 1303 is defined between the dividing wall and the remaining portion of the body 1177. A further lumen can be terminated in this passageway and is in fluid communication with the end of the connector.

It will be appreciated that fluid communication along the two passageways can be simultaneous or occur in a non-coincidental manner. For example irrigation or some other target agent can be introduced at one moment in time whilst venting and negative pressure is discontinued. The agent and/or irrigation are then stopped and negative pressure applied or reapplied.

In the case of pressure sensing this may continue continually whilst a negative pressure is applied via a separate lumen.

It will be appreciated that if irrigation fluid or a further agent are to be introduced whilst negative pressure is applied this can be achieved by having separate passageways in the body 1178 into which the multi passageway connector 1177 is introduced. For example one passageway may lead into one corner of the body 1178 whilst a further passageway is configured into an opposite corner. This will prevent the negative pressure source from sucking the introduced agent or irrigation fluid away from the wound immediately. As an alternative or in addition to having the separate passageways corresponding to the passageways in the dual lumen connector it is possible for the passageways exit orifices to be angled away from one another.

It will be appreciated that a multi passageway connector of the type illustrated in FIGS. 11 to 14 may have two, three or more passageways, each of which may connect with a respective inlet lumen arranged to perform a particular function. One, two or more passageways in the body 1178 can be provided to provide fluid communication between each inlet lumen and the target wound site.

It will be appreciated that embodiments like those illustrated with respect to FIGS. 11 to 14 may be utilised with the swivel type connector previously described. In such a case the body underlying a drape will include only one passageway or some marking or physical stop must be made on the swivel connector so that a central wall is selectively orientated at a predetermined location with respect to the body in use.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

What is claimed is:

1. An apparatus for providing fluid communication to a wound site through a drape, comprising:
    a drape having a lower adhesive surface configured to be located over the wound site;
        a drape support component located under the drape comprising:
        a lower surface configured to face the wound site;
        a top surface configured to support the drape;
        a suction port comprising an orifice in the lower surface or a side surface of the drape support component, wherein the suction port is configured to be in fluid communication with the wound site;
        a drain comprising perforations, wherein the drain is in fluid communication with the suction port; and
        a fluid passageway extending at least horizontally through the drape support component and in fluid communication with the suction port;
    a connector portion passing through the drape and having an inner lumen in fluid communication with the suction port via the fluid passageway, the connector portion extending horizontally relative to an upper surface of the drape and comprising an opening configured to receive an end of a conduit; and
    a conduit connected to the opening of the connector portion to thereby provide a fluid communication path through the drape between said conduit and the wound site.

2. The apparatus as claimed in claim 1, wherein the lower surface of the drape support component is substantially planar.

3. The apparatus as claimed in claim 1, wherein the top surface of the drape support component is substantially planar.

4. The apparatus as claimed in claim 1, wherein the drape support component comprises a peripheral lip, and wherein an outer periphery of the drape extends beyond the peripheral lip.

5. The apparatus as claimed in claim 4, wherein the peripheral lip extending circumferentially around a central raised region of the drape support component.

6. The apparatus as claimed in claim 4, wherein a shape of the peripheral lip corresponds to a shape of the drape.

7. The apparatus as claimed in claim 1, wherein the drape support component is centrally located with respect to the drape.

8. The apparatus as claimed in claim 1, wherein the drape support component has a circular shape.

9. The apparatus as claimed in claim 1, wherein the connector portion extends through an opening in the drape.

10. The apparatus as claimed in claim 1, wherein an outer diameter of the conduit corresponds to an inner diameter of the opening of the connector portion.

11. The apparatus as claimed in claim 1, wherein the suction port is a side suction port.

12. The apparatus as claimed in claim 1, further comprising gauze located under the drape and under the drape support component.

* * * * *

UNITED STATES PATENT AND TRADEMARK OFFICE
CERTIFICATE OF CORRECTION

PATENT NO. : 10,485,905 B2
APPLICATION NO. : 15/055084
DATED : November 26, 2019
INVENTOR(S) : Bannister et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 945 days.

Signed and Sealed this
Thirty-first Day of January, 2023

Katherine Kelly Vidal
*Director of the United States Patent and Trademark Office*